United States Patent
Kohli et al.

(10) Patent No.: US 9,201,027 B2
(45) Date of Patent: Dec. 1, 2015

(54) EVALUATING SEMICONDUCTOR WAFERS FOR PITCH WALKING AND/OR EPITAXIAL MERGE

(71) Applicant: International Business Machines Corporation, Armonk, NY (US)

(72) Inventors: Kriteshwar K. Kohli, Fishkill, NY (US); Patrick E. Lindo, Poughkeepsie, NY (US); Anita Madan, Danbury, CT (US); Teresa L. Pinto, Wallkill, NY (US)

(73) Assignee: GLOBALFOUNDRIES Inc., Grand Cayman (KY)

( * ) Notice: Subject to any disclaimer, the term of this patent is extended or adjusted under 35 U.S.C. 154(b) by 74 days.

(21) Appl. No.: 14/184,058

(22) Filed: Feb. 19, 2014

(65) Prior Publication Data
US 2015/0233844 A1   Aug. 20, 2015

(51) Int. Cl.
*G01N 23/20*   (2006.01)
*G03F 7/20*   (2006.01)

(52) U.S. Cl.
CPC ...... *G01N 23/20091* (2013.01); *G03F 7/70616* (2013.01)

(58) Field of Classification Search
CPC ............ G01N 21/1717; G01N 21/211; G01N 21/9501; G01N 21/95607; G01N 2021/1748; G01N 2021/216; G01N 21/171; G01N 21/21; G01N 21/8422; G01N 21/9505; G01N 21/95692; G01N 21/55; G01N 27/041; G01N 21/95684; G01N 23/20; G01N 25/07; G01N 23/20091; G01R 31/307; G01R 31/311; H01L 22/12; G01B 15/00; G03F 7/70616; G21K 1/02; G02B 27/48; G02B 19/0014; G02B 19/009; G02B 26/10; G02B 19/0085; G02B 27/095; G02B 19/0052; G02B 19/0095; G02B 19/0028; G02B 19/0057; G02B 19/0066; G02B 26/105; G02B 27/0961; G02B 27/0966; G02B 26/106; G02B 26/0875

USPC .......................................... 378/70, 71, 86, 89
See application file for complete search history.

(56) References Cited

U.S. PATENT DOCUMENTS 6,812,047 B1 * 11/2004 Borden et al. .................. 438/16
7,113,566 B1     9/2006 Peled et al.
(Continued)

FOREIGN PATENT DOCUMENTS

JP     10-048159     2/1998
JP     2006-260820   9/2006

OTHER PUBLICATIONS

"Fin stress and pitch measurement using X-ray diffraction reciprocal space maps and optical scatterometry" A. C. Diebold ; M. Medikonda ; G. R. Muthinti ; V. K. Kamineni ; J. Fronheiser ; M. Wormington ; B. Peterson ; J. Race Proc. SPIE 8681, Metrology, Inspection, and Process Control for Microlithography XXVII, 86810I (Apr. 18, 2013); doi:10.1117/12.2023081.
(Continued)

*Primary Examiner* — Irakli Kiknadze
(74) *Attorney, Agent, or Firm* — Catherine Ivers; Hoffman Warnick LLC

(57) ABSTRACT

Evaluating a semiconductor wafer may include recording a first intensity of a reflection of an X-ray beam onto a test area on a substrate of the semiconductor wafer at a detector as the X-ray beam is projected substantially perpendicular to a length of expected, periodic structures in the test area and at an angle defined between the X-ray beam and a surface of the test area. Second intensities may be recorded of the reflection of the X-ray beam onto the test area as the X-ray beam is projected onto the test area at increments from the angle. Intensity peaks in the recordings of the first and second intensities are identified and, based on positions of the intensity peaks relative to the test area, a peak spacing between the plurality of expected, periodic structures is determined indicative of pitch walking or epitaxial merge.

20 Claims, 10 Drawing Sheets

(56) References Cited

U.S. PATENT DOCUMENTS

| | | | |
|---|---|---|---|
| 7,875,850 B2 | 1/2011 | Nakayama et al. | |
| 2002/0125905 A1* | 9/2002 | Borden et al. | 324/765 |
| 2002/0151092 A1* | 10/2002 | Li et al. | 438/16 |
| 2004/0120459 A1 | 6/2004 | Crowley et al. | |
| 2009/0239314 A1* | 9/2009 | Haberjahn et al. | 438/8 |
| 2012/0014508 A1 | 1/2012 | Wormington et al. | |
| 2012/0244711 A1 | 9/2012 | Yin et al. | |

OTHER PUBLICATIONS

"International Technology Roadmap for Semiconductors Metrology Roadmap 2012" Metrology Technical Working Group Alain Diebold (CNSE); Christina Hacker (NIST).

* cited by examiner

EVALUATING SEMICONDUCTOR WAFERS FOR PITCH WALKING AND/OR EPITAXIAL MERGE

BACKGROUND

1. Technical Field

The disclosure relates generally to semiconductor wafer metrology, and more particularly, to a system for evaluating a semiconductor wafer and detecting pitch walking and/or epitaxial merge.

2. Background Art

Integrated circuit (IC) chips are formed on semiconductor wafers at increasingly smaller scale. In current technology nodes, such as 7, 10 and 14 nanometer technologies, transistor devices are constructed as three-dimensional (3D) fin field effect transistor (FINFET) structures. As shown in the scanning electron microscope (SEM) image of FIG. 1, the fins of the FINFETS are expected to be constructed as repeating, equally spaced, vertical structures on the wafer. Equally spaced gates are formed as repeating vertical structures that overlay the fins in an orthogonal direction.

A challenge in constructing the repeating structures such as fins and gates at these advanced technology nodes is that variability in pitch spacing between the structures and pitch walking can occur during the formation of the structures using current sidewall image transfer (SIT) photolithography techniques. "Pitch walking" is a condition, as shown in the SEM image of FIG. 2, in which expected, periodic structures, e.g., fins as shown, are constructed with unequal spacing and different periodicities. In the example shown, the fins are paired with members of each pair closer together than they are to an adjacent pair, resulting in a non-uniform pitch across all of the structures. In some instances, adjacent fins and/or gates may merge into a single structure. Pitch walking can occur relative to fins and at the gate patterning level, and is detrimental to device yield. In addition to fins and gates, in subsequent processing, epitaxial films are deposited on the fins. Avoiding merging of epitaxially grown structures ("epi merge") is a key metric for device performance targets. Since SIT photolithography techniques will be implemented in the above-identified technology nodes, pitch tolerance will be important for accurately constructing devices, e.g., landing contacts on gates. In this regard, pitch walking tolerance requirements are anticipated to be +/−1 nanometer (nm).

Tolerances of +/−1 nm, however, are below the sensitivity of existing metrology techniques, and so the ability to detect pitch walking has become more difficult as the critical dimensions (CDs) and pitch spacing shrink. In particular, traditional in-line measurement techniques (e.g., critical dimension scanning electron microscope (CDSEM)) do not have the precision and the capability to determine the pitch walking at the requisite size, e.g., on the order of 1 nm. CDSEM techniques are also difficult to implement because the structures that exist at such small CDs exhibit line edge roughness that complicates measurements. Optical reflectometry-based scatterometric techniques are also problematic because they are model based, use data that can be convoluted by any underlying topography and films, and are generally unproven.

BRIEF SUMMARY

A first aspect of the disclosure provides a method of evaluating a semiconductor wafer, the method comprising: recording a first intensity of a reflection of an X-ray beam onto a test area on a substrate of the semiconductor wafer at a detector, the recording occurring as the X-ray beam is projected substantially perpendicular to a length of a first plurality of expected, periodic structures in the test area and at an angle defined between the X-ray beam and a surface of the test; recording a plurality of second intensities of the reflection of the X-ray beam onto the test area as the X-ray beam is projected onto the test area at a plurality of increments from the angle; and identifying intensity peaks in the recordings of the first and second intensities and, based on positions of the intensity peaks relative to the test area, determining a peak spacing between two adjacent peaks of the plurality of expected, periodic structures.

A second aspect of the disclosure provides a system for evaluating a semiconductor wafer, the system comprising: a computing device for: receiving a recording of a first intensity of a reflection of an X-ray beam onto a test area on a substrate of the semiconductor wafer, the recording occurring as the X-ray beam is projected substantially perpendicular to a length of a first plurality of expected, periodic structures in the test area and at an angle defined between the X-ray beam and a surface of the test area; receiving a recording of a plurality of second intensities of the reflection of the X-ray beam onto the test area as the X-ray beam is projected onto the test area at a plurality of increments from the angle; and identifying intensity peaks in the recordings of the first and second intensities and, based on positions of the intensity peaks relative to the test area, determining a peak spacing between two adjacent peaks of the plurality of expected, periodic structures.

A third aspect of the disclosure provides a program product stored on a computer-readable medium, which when executed, evaluates a semiconductor wafer, the program product comprising: program code for recording a first intensity of a reflection of an X-ray beam onto a test area on a substrate of the semiconductor wafer at a detector, the recording occurring as the X-ray beam is projected substantially perpendicular to a length of a first plurality of expected, periodic structures in the test area and at an angle defined between the X-ray beam and a surface of the test area; program code for recording a plurality of second intensities of the reflection of the X-ray beam onto the test area as the X-ray beam is projected onto the test area at a plurality of increments from the angle; and program code for identifying intensity peaks in the recordings of the first and second intensities and, based on positions of the intensity peaks relative to the test area, determining a peak spacing between two adjacent peaks of the plurality of expected, periodic structures.

A fourth aspect of the invention includes a method of evaluating a semiconductor wafer comprising: detecting pitch walking amongst a plurality of expected, periodic, vertical structures on a test area of the semiconductor wafer within a range of less than approximately +/−1.0 nanometers.

The illustrative aspects of the present disclosure are designed to solve the problems herein described and/or other problems not discussed.

BRIEF DESCRIPTION OF THE DRAWINGS

These and other features of this disclosure will be more readily understood from the following detailed description of the various aspects of the disclosure taken in conjunction with the accompanying drawings that depict various embodiments of the disclosure, in which.

It is noted that the drawings of the disclosure are not to scale. The drawings are intended to depict only typical aspects of the disclosure, and therefore should not be considered as limiting the scope of the disclosure. In the drawings, like numbering represents like elements between the drawings.

DETAILED DESCRIPTION

As indicated above, the disclosure provides evaluation of a semiconductor wafer for pitch walking and/or epitaxial merge, which may be indicated as a defect. Embodiments of the disclosure employ high resolution X-ray diffraction (HRXRD) techniques for quantification of the pitch and pitch walking for a plurality of expected, periodic vertical structures, such as FINS, gates, or overlaying epitaxial structures, at any processing level. As will be described, embodiments of the disclosure record appropriate scans at specific orientations relative to a test area including the expected, periodic structures. HRXRD scans are sensitive to the crystalline material of the substrate (e.g., silicon, silicon germanium, germanium, gallium arsenide, etc.) and any epitaxial layers thereon, e.g., silicon germanium on silicon. Consequently, HRXRD techniques described herein are applicable to any form of crystalline material. HRXRD techniques described herein can also be used to determine whether the expected, periodic structures are merged or not. Also, HRXRD techniques can be used to determine the "pitch walking" of periodic structures (amorphous, poly crystalline or otherwise) which are surrounded by crystalline materials. The technique described is non-destructive and non-contact, and is un-convoluted with the dimensions (CD, height, etc.) of the three-dimensional structures.

Embodiments of the invention determine peak spacing between peaks in recorded intensities of reflections of structure on the test area. The recorded peaks can be used to calculate a pitch of the expected, periodic structures. Pitch (or pitch spacing) is defined as the distance between repeated elements in a structure possessing translational symmetry (e.g., the distance between repeated fins). If certain vertical structures such as fins are not equally spaced and have different periodicities, there is pitch walking. If the pitch walking is beyond an acceptable level, a defect may be indicated and adjustments to a tool made to manufacture it, e.g., a photolithography tool, can be made to correct for the defect. Alternatively, where peak spacing indicates that only one peak exists, it is indicative of epitaxial merge, the presence of which may be a defect depending on the process of record.

Figure 3:
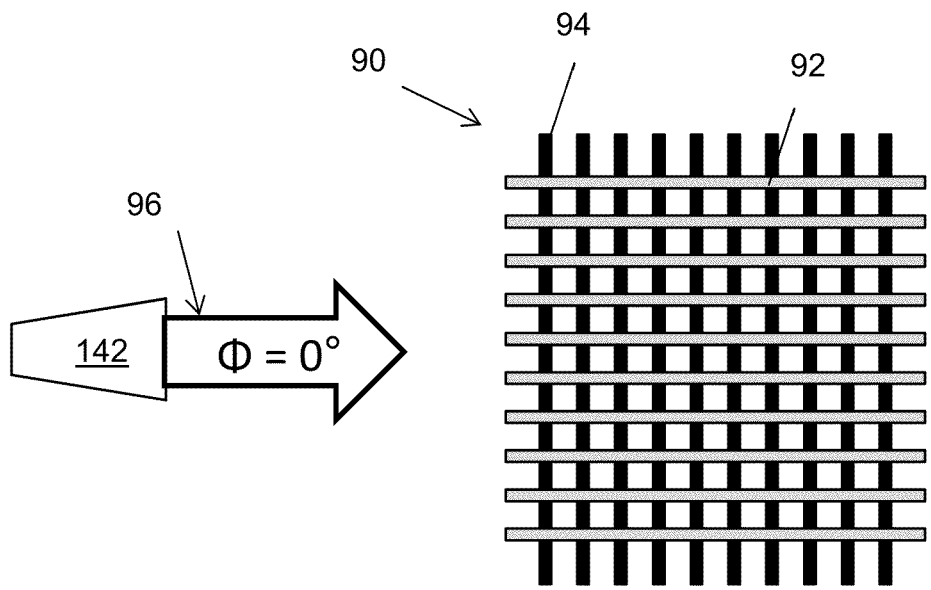
FIG. 3 shows an angle of an X-ray beam projection to a test area during one sub-step of a method according to embodiments of the invention.
Figure 4:
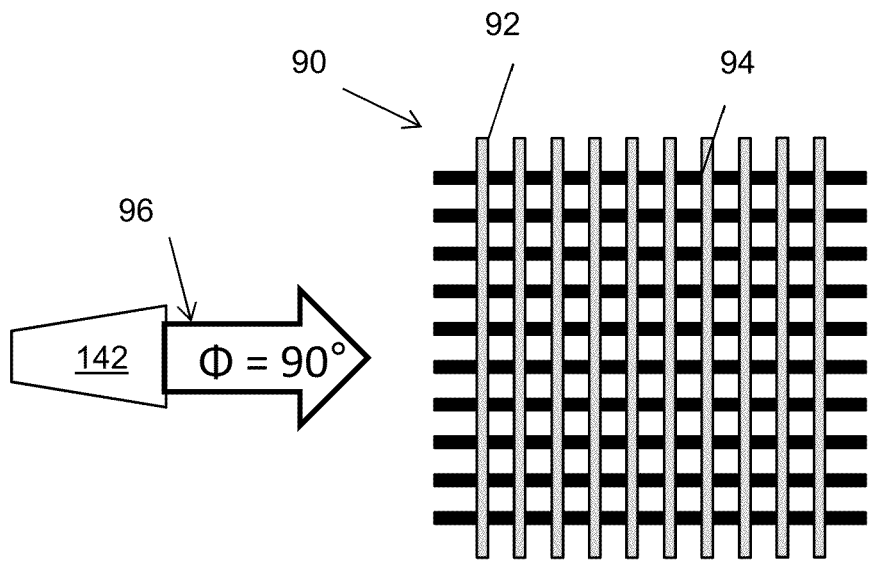
FIG. 4 shows an angle of an X-ray beam projection to a test area during one sub-step of a method according to embodiments of the invention.

As will be described in greater detail herein, as shown in FIGS. 3-4, embodiments of the disclosure employ a specially designed test area 90, i.e., macro, including a first plurality of expected, periodic structures 92 (lighter shading) in the form of fins and a second plurality of expected, periodic structures 94 (darker shading) in the form of gates, e.g., polysilicon, extending perpendicularly across the first plurality of structures. Test area 90 may be constructed using any now known or later developed semiconductor processing techniques, e.g., deposition, patterning, etching, etc. Test area 90 may also have epitaxial structures formed over the fins and/or gates. In this case, the epitaxial structures would appear the same as fins 92, and hence they are not separately labeled. As used herein, "expected, periodic structures" are structures that are anticipated to be generated, e.g., using inter alia photolithography tool 132 (FIG. 5) and epitaxy deposition tool 134 (FIG. 5), such that they are equally spaced or periodically arranged on the semiconductor wafer. As will be described herein in greater detail, FIG. 3 shows test area 90 (wafer) turned at a first impinging angle $\Phi$ of 0° such that X-ray beam 96 (projected from generator 142) impacts gates 94 substantially perpendicularly, and FIG. 4 shows test area 90 at a second impinging angle $\Phi$ of 90° such that X-ray beam 96 impacts fins 92 substantially perpendicularly.

Figure 5:
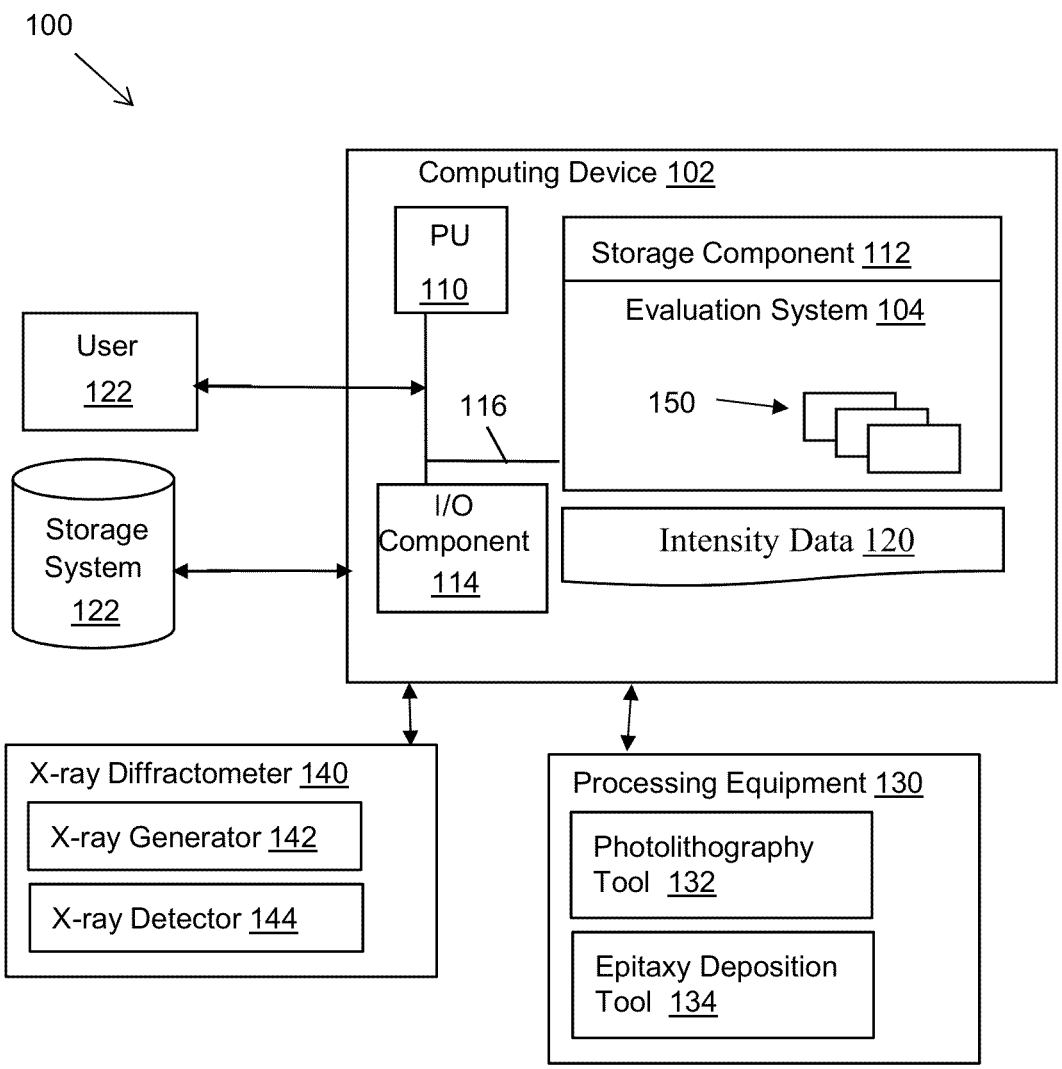
FIG. 5 shows a block diagram of an environment for evaluating a semiconductor wafer according to embodiments of the invention.

FIG. 5 shows an illustrative environment 100 for evaluating a semiconductor wafer according to embodiments of the disclosure, operation of which will be described relative to FIGS. 6-7.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Continuing with FIG. 5, an illustrative environment 100 for evaluating a semiconductor wafer according to embodiments of the disclosure is shown. Environment 100 includes at least one computing device 102 including an evaluation system 104 that can perform processes described herein in order to evaluate a semiconductor wafer.

Computing device 102 is shown including a processing component 110 (e.g., one or more processors), a storage component 112 (e.g., a storage hierarchy), an input/output (I/O) component 114 (e.g., one or more I/O interfaces and/or devices), and a communications pathway 116. In general, the processing component 110 executes program code, such as evaluation system 104, which is at least partially fixed in storage component 112. While executing program code, the processing component 110 can process data, such as X-ray intensity data 120 and/or the like, which can result in reading and/or writing transformed data from/to the storage component 112 and/or the I/O component 114 for further processing. Pathway 116 provides a communications link between each of the components in computing device 102. I/O component 114 can include one or more human I/O devices, which enable a human user 122 to interact with computing device 102 and/or one or more communications devices to enable a system user 122 to communicate with the computing device 102 using any type of communications link. To this extent, evaluation system 104 can manage a set of interfaces (e.g., graphical user interface(s), application program interfaces, and/or the like) that enable human and/or system users 122 to interact with evaluation system 104. Furthermore, evaluation system 104 can manage (e.g., store, retrieve, create, manipulate, organize, present, etc.) the data, such as intensity data 120 and/or the like, using any solution. As described herein, computing device 102 may be part of a semiconductor fabrication system that may include a large number of semiconductor processing equipment 130, including for example, a photolithography tool 132. As also described herein, computing device 102 is operably coupled to an X-ray diffractometer 140 including an X-ray generator 142, goniometer and a detector 144. Intensity data 120 may include data about the diffracted intensities as detected by detector 144. Intensity data 120 may be obtained from a data log, model, and/or from real-time communication with X-ray detector 144 (via wireless and/or hard-wired means). Intensity data 120 can also include data transmitted by evaluation system 104, e.g., instructing photolithography tool 132 to make an adjustment.

Computing device 102 can include one or more general purpose computing articles of manufacture (e.g., computing devices) capable of executing program code, such as evaluation system 104, installed thereon. As noted above, evaluation system 104 can be embodied as any combination of system software and/or application software. Furthermore, as noted herein, evaluation system 104 can be implemented using a set of modules 150. In this case, a module 150 can enable computing device 102 to perform a set of tasks used by evaluation system 104, and can be separately developed and/or implemented apart from other portions of system 104. As used herein, the term "module" means program code that enables a computing device 102 to implement the actions described in conjunction therewith using any solution. When fixed in a storage component 112 of a computing device 102 that includes a processing component 110, a module implements the actions. Regardless, it is understood that two or more modules, and/or systems may share some/all of their respective hardware and/or software. Furthermore, it is understood that some of the functionality discussed herein may not be implemented or additional functionality may be included as part of computing device 102.

When computing device 102 includes multiple computing devices, each computing device can have only a portion of evaluation system 104 fixed thereon (e.g., one or more modules 150). However, it is understood that computing device 102 and evaluation system 104 are only representative of various possible equivalent computing devices that may perform a process described herein. To this extent, in other embodiments, the functionality provided by computing device 102 and evaluation system 104 can be at least partially implemented by one or more computing devices that include any combination of general and/or specific purpose hardware with or without program code. In each embodiment, the hardware and program code, if included, can be created using standard engineering and programming techniques, respectively.

When computing device 102 includes multiple computing devices, the computing devices can communicate over any type of communications link. Furthermore, while performing a process described herein, computing device 102 can communicate with one or more other computing devices using any type of communications link, e.g., in diffractometer 140 or other processing equipment 130. In either case, the communications link can include any combination of various types of optical fiber, wired, and/or wireless links; include any combination of one or more types of networks; and/or utilize any combination of various types of transmission techniques and protocols.

Figure 6:
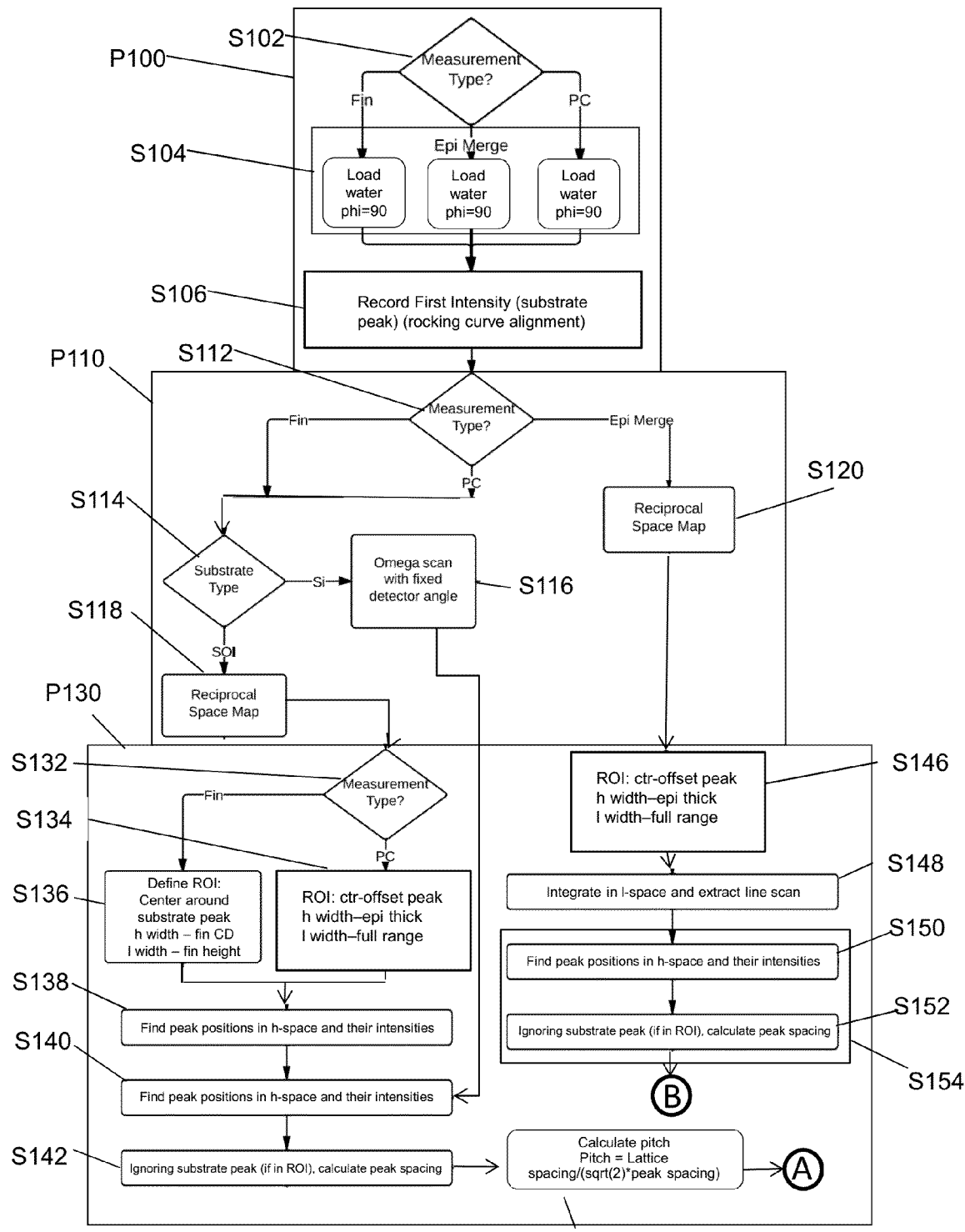
FIGS. 6-7 show a flow diagram illustrating an embodiment of an operational methodology according to embodiments of the invention.
Figure 7:
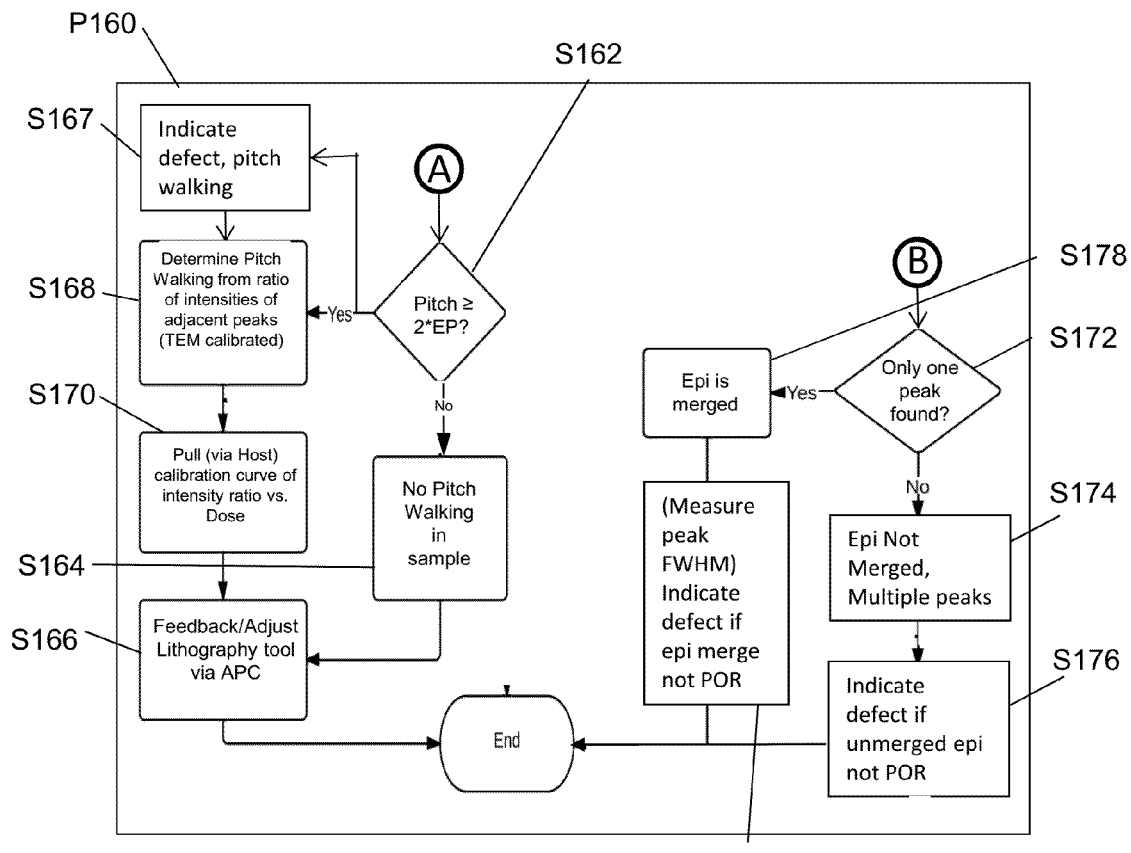

Referring to FIGS. 6 and 7, a flow diagram illustrating an embodiment of operation of evaluation system 104 is illustrated. The flow diagram will be described in conjunction with FIGS. 3-4 and 8-13.

Figure 8:
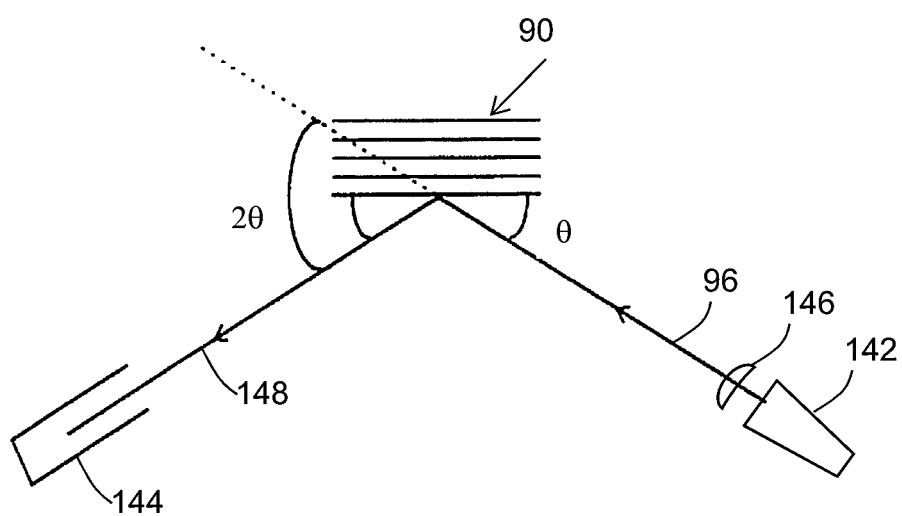
FIG. 8 shows projecting of an X-ray beam on a test area according to embodiments of the invention.

X-ray diffractometer 140 (labeled only in FIG. 5) may include any now known or later developed high resolution X-ray diffractometer (HRXRD). As shown in FIG. 8 and as understood, diffractometer 140 includes an X-ray generator 142 and an X-ray detector 144. Generator 142 creates an X-ray beam 96 that is preferably monochromatic (conditioned) and collimated; however, such characteristics may not be necessary in all instances. The collimated X-ray beam 96 may be produced using any solution, such as a 2-bounce or a 4-bounce crystal 146 in the beam path. Detector 144 may include any now known or later developed detector such as but not limited to: a scintillation detector and a crystal or a one-dimensional (1D) detector, capable of collecting and recording the diffracted beam 148 intensity. A 1D detector may act to speed up the measurement where full reciprocal space maps (RSM) are collected, as will be described herein. As used herein, recording "intensity" indicates recording a range of intensities of a reflection from test area to ensure capturing a highest intensity or peaks within the range of intensities.

With reference to FIGS. 3-5, process P100 includes evaluation system 104 recording a first intensity of a reflection of an X-ray beam onto test area 90 on a substrate of the semiconductor wafer at detector 144. In one embodiment, this process includes generator 142 impinging X-ray beam 96, as shown in FIGS. 3-4, substantially perpendicular to a length of a first plurality of expected, periodic structures 92 or 94 in test area 90 and at an angle $\Theta$, as shown in FIG. 8, defined between X-ray beam 96 and a surface of the test area 90. The initial angle $\Theta$ may be dependent on a type of the substrate. In this fashion, the first intensity represents a maximum reflection from test area 90 (FIGS. 3, 4) at a center location of test area 90. The recording of the first intensity may be referred to herein as the "substrate peak" as it represents a centered, maximum peak in the recordings (see FIGS. 9 and 10), as will be described herein. Computing device 102 may receive first intensity recordings from detector 144, i.e., from intensity data 120 or directly there from in real time.

As shown in FIG. 8, angle $\Theta$ may be referred to herein as an incident angle as it is defined between X-ray beam 96 and a surface of test area 90. Relative to FIGS. 3-4, angle $\Theta$ is the angle at which generator 142 is positioned relative to the surface of the page. Although not necessary in all cases, the desired angle $\Theta$ may be made to depend on a type of the crystalline material of the substrate of the semiconductor wafer (or a crystalline layer thereover), e.g., bulk silicon, silicon-germanium, silicon-on-insulator (SOI), gallium arsenide, etc., because the different substrates may require different angles to attain better, more accurate reflection data. For example, in one embodiment, for a bulk silicon substrate, angle $\Theta$ may be selected from the group consisting of approximately 34.5° (004), approximately 56.1° (113) and approximately 79.3° (224), as these angles are a sample of the allowed reflections from silicon. For silicon-germanium, angles are lower than silicon and depend on the germanium Ge fraction. Other crystalline material may require a different incident angle $\Theta$.

As indicated by sub-steps S102 and S104, the different orientations of expected, periodic structures determine at which angle $\Phi$ (between projected beam and length of structures 92 or 94 on test area 90) the first intensity is recorded. In sub-step S102, evaluation system 104 determines what type of structure is being evaluated. The type of expected, periodic structure to be evaluated may be user defined, or otherwise determined from simple observation of test area 90, e.g., using an SEM. Evaluation system 104 may operate on any expected, periodic structure between or on crystalline material. For purposes of description, three types of expected, periodic structures are evaluated: fins 92, gates 94 (referred to in flow as "PC" for gate conductor) or epitaxial structures (also 92 in FIGS. 3-4) formed on/over the fins and running in the same direction as fins 92. (Although aggressive pitch walking can also cause partial merge, generally epitaxial structures may have epitaxial merge issues, while fins and gates may have pitch walking issues). In sub-step S102, evaluation system 104 determines whether the expected, periodic structures are in the form of fins 92, gates 94 (PC) or epitaxial structure. Depending on the type of structure to be measured, at sub-step S104, evaluation system 104 provides diffractometer 140 with the required angle Φ (FIGS. 3, 4) to be employed for recording the first intensity, i.e., the angle at which generator 142 will impinge X-ray beam 96 onto a length of structures of test area 90. (As used herein, the angle at which X-ray beam 96 impinges a length of structures in test area 90 is Φ. The angle between X-ray beam 96 and the substrate surface of test area 90 is θ). In particular, for fins 92 or epitaxial structures ("epi merge"), test area 90 (wafer) is turned at a first impinging angle Φ of 90° such that X-ray beam 96 impacts fins 92 or epitaxial structures thereon substantially perpendicularly. In contrast, for gates 94, test area 90 (wafer) is turned at a first impinging angle Φ of 0° such that X-ray beam 96 impacts gates 94 substantially perpendicularly.

In sub-step S106, recording of first intensity occurs. In one embodiment, an incremental movement of test area 90 from the substantially perpendicular position (i.e., angle Φ)(and also angle Θ) may be carried out to ensure the first intensity (substrate peak) is recorded (referred to in sub-step S106 as "rocking curve alignment"). The rocking curve alignment of sub-step S106 may not be necessary in all instances, e.g., where a substrate peak is readily obtained without moving test area 90 or detector/generator. The incremental changes may occur in positive, negative and/or positive and negative directions. In addition, the incremental changes may be in the range of, for example, +/−0.2-0.5°, and the number of increments may be user defined to ensure capture of a region near the substrate peak.

Although described as though test area 90 is rotated to attain the stated angle, it is understood that either semiconductor wafer (test area 90) and/or generator 142 and/or detector 144 may be rotated to attain the desired angles. In any event, the recording by detector 144 occurs as the X-ray beam is projected. First intensity recording data may be stored by evaluation system 104 as intensity data 120 (FIG. 5).

Returning to FIG. 6, as will be described, process P110 includes evaluation system 104 recording a plurality of second intensities of the reflection of X-ray beam 96 onto test area 90 as the X-ray beam is projected onto the test area at a plurality of increments from an angle Θ (FIG. 8). As will be described, each second intensity is created by a reflection from a corresponding expected, periodic structure, e.g., fin. Consequently, each recorded second intensity is representative of the expected, periodic structures. The second intensities when recorded and graphically represented relative to the first intensity (substrate peak) and other second intensities ought to indicate equal spacing representative of the equal spacing between expected, periodic structures, e.g., fins. When spacing is not equal amongst the second intensities, depending on the structures being evaluated, either pitch walking or epitaxial merge is indicated. As will be described, the recording of the plurality of second intensities may include positioning detector 144 at a detector angle relative to X-ray beam 96 that is twice that of an incident angle of the X-ray beam on the test area, and incrementally changing at least one of the angles to maximize each second intensity at the detector. Computing device 102 may receive second intensity recordings from detector 144, i.e., from intensity data 120 or directly there from in real time.

As shown in FIG. 6, different types of recording and subsequent processing may be carried out by evaluation system 104 depending on the measurement type, e.g., fins, gates (PC) or epitaxial structure ('epi merge'). That is, although the general processes P110, P120, S130, P160 (latter in FIG. 7) remain the same for all structures, the particular sub-steps within each process may vary depending on the type of structure to be evaluated. In particular, sub-steps within each process P110, P120, P130, P160 (latter in FIG. 7) can follow two general different paths for fins and gates versus that for epitaxial structure merge. The flow for fin 92 and gate 94 (PC) evaluation appears generally on the bottom, left side of FIG. 6 and the left side of FIG. 7, while that for epitaxial structures ('epi merge') evaluation appears generally on the bottom, right side of FIG. 6 and the right side of FIG. 7.

Continuing with the description of the flow, in sub-step S112, evaluation system 104 determines what type of structure is being measured. As noted herein, three types of expected, periodic structures can be evaluated: fins 92, gates 94 or epitaxial structures (also 92) formed on/over the fins and running in the same direction as fins 92. In sub-step S112, evaluation system 104 determines whether the expected, periodic structures are in the form of fins 92, gates 94 (PC) or epitaxial structure on top of the fins. As described herein, the type of expected, periodic structure to be evaluated may be user defined, or may be observed from test area 90, e.g., using an SEM.

Turning first to processing for fins and gates, at sub-step S114, evaluation system 104 may determine the type of substrate upon which test area 90 is formed. "Substrate" may include the actual substrate or a top layer(s) thereover, the latter of which can be any form of crystalline material. This information may be user defined or readily discernible from test area 90 through routine inspection. As noted above, process P110 includes, as shown in FIG. 8, evaluation system 104 recording a plurality of second intensities of the reflection of X-ray beam 96 onto test area 90 as the X-ray beam is projected onto the test area at a plurality of increments from an angle Θ. As noted above, angle Θ may be referred to herein as an incident angle as it is defined between X-ray beam 96 and a surface of test area 90, i.e., an angle of generator 142 projects beam 96 relative to surface of paper in FIGS. 3-4. Although not necessary in all cases, the desired angle Θ may be made to depend on a type of the crystalline material of the substrate of the semiconductor wafer, e.g., bulk silicon, silicon-germanium, silicon-on-insulator (SOI), gallium arsenide, etc., because the different substrates may require different angles to attain better, more accurate reflection data. For example, where the substrate includes a bulk silicon substrate, at sub-step S116, evaluation system 104 may conduct a scan with generator 142 and detector 144 starting at specified angles, and incrementally changing generator incident angle Θ while recording second intensities at detector 144. This scan is referred to in the drawing as an 'omega scan with fixed detector angle'. In this case, as noted above, in one embodiment, angle Θ may be selected from the group consisting of approximately 34.5° (004), approximately 56.1° (113) and approximately 79.3° (224), as these angles are a sample of the allowed reflections from silicon. For a different substrate, a different incident angle Θ may be employed. The increments from angle Θ can be user defined, but are such that any maximum intensity peak can be recorded in a confident manner for each second intensity. In one example, the increments can be in the range of +/−0.2-0.5°. The incremental changes may occur in positive, negative and/or positive and negative directions (i.e., +/−), and the number of increments can be user defined such that the recording by detector 144 of the plurality of second intensities includes recording a highest intensity within each of the plurality of second intensities to ensure a peak is discernible. In one embodiment, as shown in FIG. 8, the recording of the plurality of second intensities may include positioning detector 144 at a detector angle relative to the X-ray beam that is twice that of an incident angle Θ of the X-ray beam 96 on test area 90. In this case, recording the plurality of second intensities may include the above-described positioning, and incrementally changing at least one of the angles Θ or detector angle (noted as $2Θ_B$) to maximize each second intensity at the detector. That is, during detection, evaluation system 104 may incrementally change at least one of the angles to maximize each second intensity at the detector 144. For example, an incident angle Θ of X-ray beam 96 from generator 142 can incrementally changed from Θ to maximize each second intensity at the detector, i.e., to ensure that a peak for each second intensity is recorded indicative of the structure reflecting the X-ray beam. Once sub-step S116 is complete, processing may proceed to sub-step S140, described hereafter.

Figure 14:
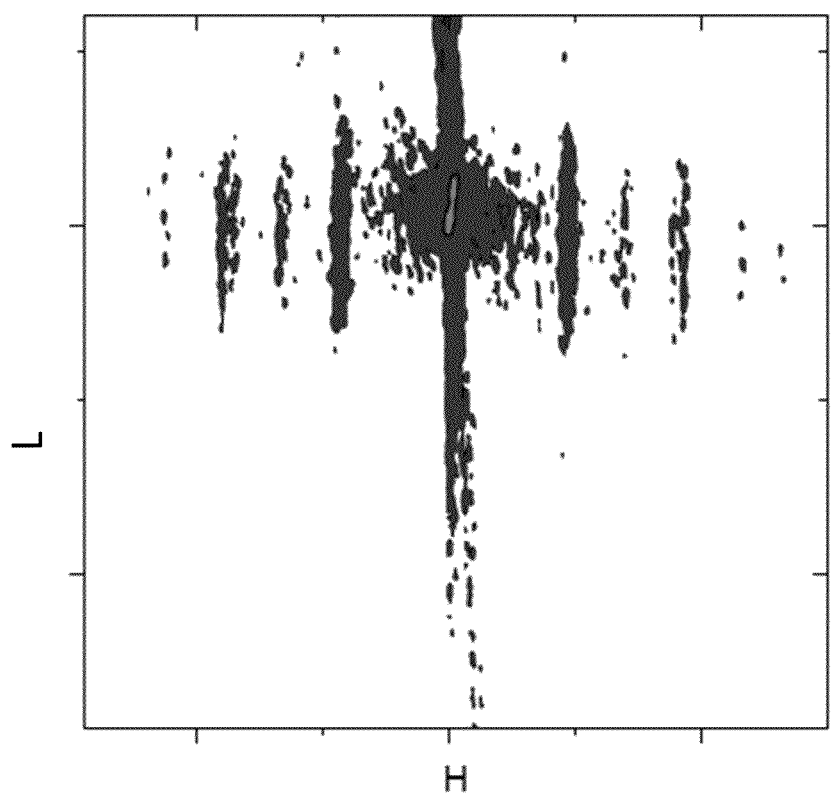
FIG. 14 shows an illustrative reciprocal space map according to embodiments of the invention.

Referring again to sub-step S114, where the substrate includes SOI, i.e., SOI at sub-step S114, at sub-step S118 evaluation system 104 performs a series of scans at slightly different angle Θ increments. These scans are then stitched together to form a reciprocal space map (RSM). The x and y are subsequently converted into dimensionless units 'h' and 'k' using the equations described in "High-Resolution X-Ray Scattering: From Thin Films to Lateral Nanostructures" by Pietsch et al., 2004. As shown in FIG. 14, this sub-step generates a reciprocal space map (RSM) with recorded intensity plotted as a 3D map with h and k as the x and y axis, respectively, and intensity as the z axis (based on brightness in image—see legend, typically by use of color). Once sub-step S118 is complete, processing may proceed to sub-step S132 in process P130, described hereafter.

With further regard to sub-steps S114 and S116, while a particular type of test, i.e., RSM or omega scan, has been described relative to a particular type of substrate, it is emphasized that the types of scans are not exclusive to the type of substrate and, if desired, RSM can be used with a silicon substrate and an omega scan can be used with SOI. Minor adjustments may be made to accommodate the different substrates, and record the second intensities as required. Where different scans based on substrate type are not desired, sub-step S114 may be omitted.

Returning to sub-step S112 of process P110, where evaluation system 104 determines the type of structure that is being measured to be epitaxial structures, at sub-step S120, evaluation system 104 performs an RSM, as described above.

With reference to sub-steps S116, S118 and S120, although described as though generator 142 is rotated to attain the stated angle, it is understood that either semiconductor wafer (test area 90) and/or generator 142 and/or detector 144 may be rotated to attain the desired angles. In any event, the recording by detector 144 occurs as the X-ray beam is projected, and the second intensities may be recorded (and stored) by evaluation system 104 as intensity data 120 (FIG. 5).

Continuing with FIG. 6, process P130 includes evaluation system 104 identifying intensity peaks in the recordings of the first and second intensities and, based on positions of the intensity peaks relative to the test area, and determining a peak spacing between two adjacent peaks of the plurality of expected, periodic structures. As will be described, for epitaxial structures that have merged, the "determining a peak spacing" may indicate that no spacing between peaks exist, i.e., where epitaxial merge exists.

Figure 9:
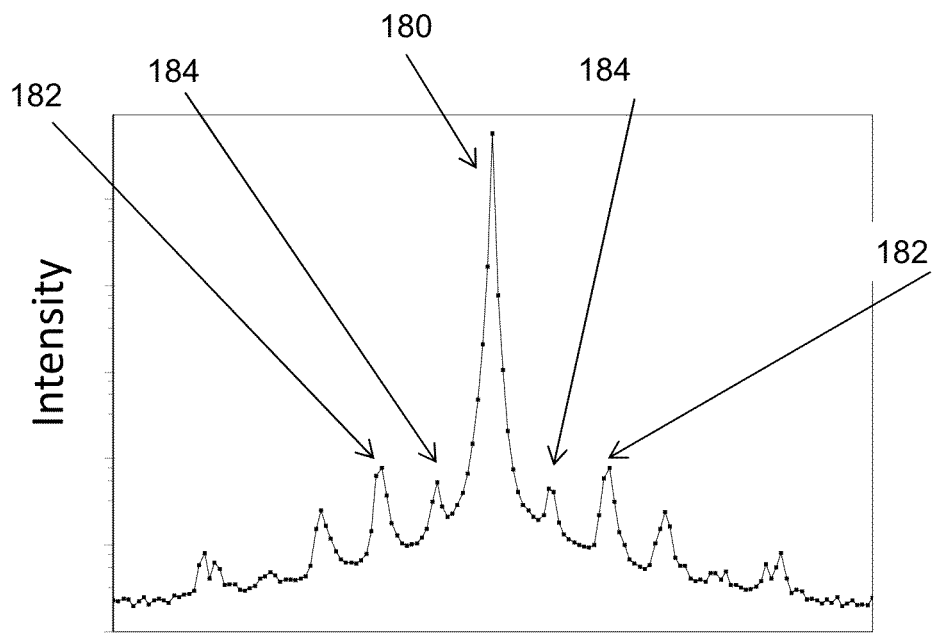
FIG. 9 shows an illustrative graphical representation of peak intensities recorded from a detector for a silicon-based substrate having structures exhibiting pitch walking according to embodiments of the invention.
Figure 10:
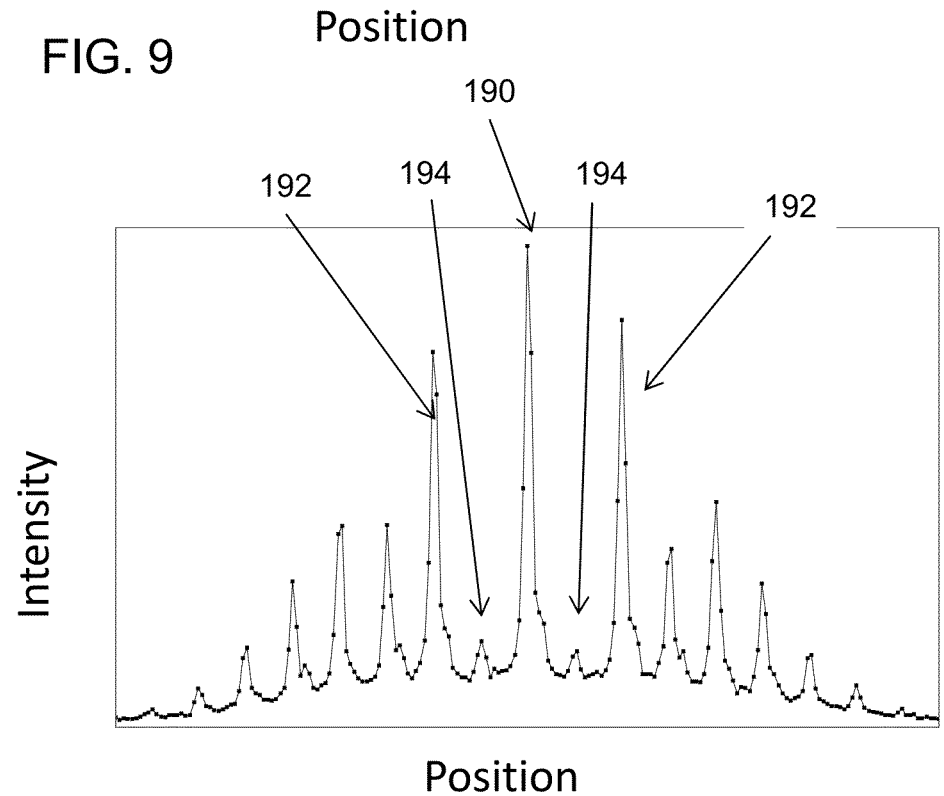
FIG. 10 shows an illustrative graphical representation of peak intensities recorded from a detector for a substrate having epitaxial structures exhibiting pitch walking according to embodiments of the invention.

Referring to processing for fins and gates on the bottom, left side of FIG. 6, different intensity peaks result from different expected, periodic structures such that different techniques must be used to identify the peak intensities based on the structures being evaluated. To this end, in sub-step S132, evaluation system 104 determines the type of measurement, e.g., fins or gates (PC), such that at sub-steps S134, S136, a relevant region of interest (ROI) from an RSM of test area 90 can be identified for each, i.e., within recording data of first and second intensities. For gates, at sub-step S134, the ROI of test area 90 can be centered around an "offset peak," which is defined by the expected atomic concentration of the substitutional atom in the deposited epitaxial film, and may be include a single or multiple peaks. In this case, the ROI should be selected such that width in h-space is representative of epitaxial thickness, and width in l-space can be the measured range in l. In contrast, at sub-step S136, for fin structures, the ROI of test area 90 can be centered around the first intensity (substrate peak). In this case, the ROI should be selected such that width of ROI in h-space is representative of expected fin critical dimension (CD) and width of ROI in L-space width captures expected fin height. Subsequent integration (i.e. integration in h-space) across one fin peak and fitting of such peak provides measure of fin height. Fitting of the envelope of fin peaks post integration in l-space provides a measure of fin CD. For example, in sub-step S138, the data is integrated in the l-space and the recordings (line scan) are extracted from the ROI. FIGS. 9 and 10 show two illustrative graphical representations of the recordings of the first and second intensities, i.e., data integrated in l-space or omega scans and recordings extracted. Each graph plots the diffracted intensity relative to test area 90 against h or angle depending on the units used. FIG. 9 shows data for fins in test area 90 having a silicon substrate and exhibiting pitch walking in the fins. As shown in FIG. 9, the first intensity (substrate peak) 180 is positioned at the center of the graph, and peaks 182, 184 occur on each side thereof. As will be described, peaks 182 are indicative of expected, periodic structures, and smaller peaks 184 indicate pitch walking, i.e., structures on test area 90 are reflecting from locations at which equally spaced structures would not exist. Where no pitch walking is present, only peaks 182 would exist. In contrast, FIG. 10 shows data for gates in test area 90 having a silicon-germanium fins and exhibiting pitch walking. As shown in FIG. 10, the first intensity is positioned at the offset peak of the graph, and peaks occur on each side thereof. As shown in FIG. 10, the first intensity 190 is at the center of the graph, and peaks 192, 194 occur on each side thereof. Similar to FIG. 9, peaks 192 are indicative of expected, periodic structures, and smaller peaks 194 indicate pitch walking Where no pitch walking is present, only peaks 192 would exist.

Returning to FIG. 6, in sub-step S140 (from which processing from sub-step S138 or S116 may proceed), peak positions in the h-space and their intensities are found, i.e., from the intensity data as represented in the graphical representations of FIGS. 9 and 10. In sub-step S142, the peak spacing is calculated (determined), ignoring the first intensity (substrate peak) if it is in the ROI. As can be discerned by evaluating the graphs of FIGS. 9 and 10, peak spacing can be readily determined (Δh is the position difference between fin peaks in hkl units) based on the position relative to test area 90.

Figure 11:
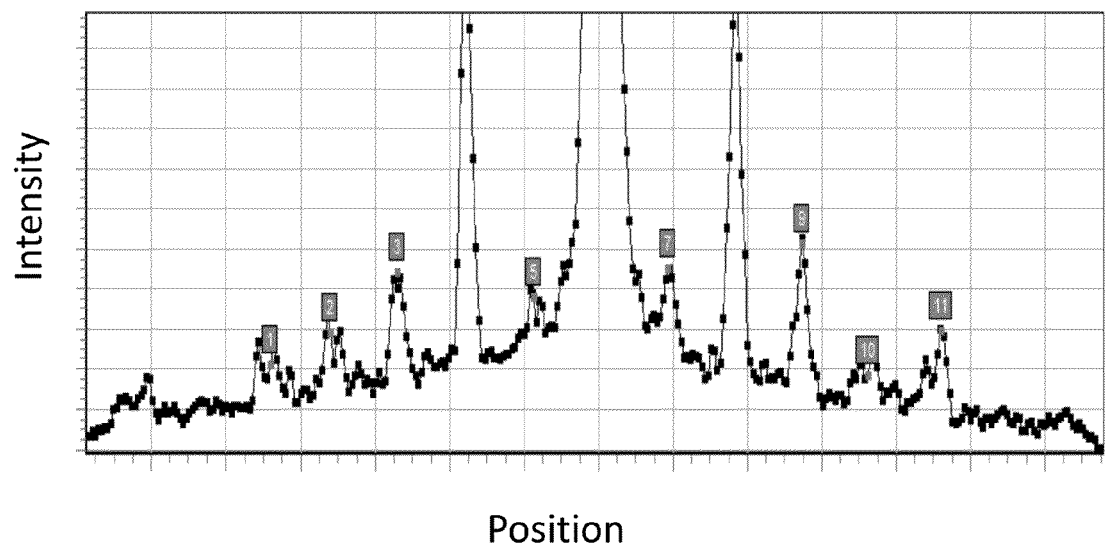
FIG. 11 shows an enlarged illustrative graphical representation of peak intensities recorded from a detector for structures exhibiting pitch walking according to embodiments of the invention.

In sub-step S144, evaluation system 104 may determine a pitch based on the peak spacing. This sub-step may include automatically calculating (determining) the pitch based on a mathematical calculation based on an average peak spacing. More specifically, FIG. 11 shows an illustrative graphical representation of an integrated number of peaks numbered 1-11 (peaks 4 and 8 are out of the graph window; the first intensity (substrate peak) is not numbered). Evaluation system 104 may calculate an average peak spacing by averaging a distance between a plurality of adjacent peaks, e.g., peaks 2-3, 7-8, 8-9, 10-11, etc. Any number of desired pairings may be employed. Evaluation system 104 may then calculate the pitch according to the following formula:

$$\text{pitch} = \left( \frac{\text{lattice spacing}}{\sqrt{2} * \text{average peak spacing}} \right),$$

where lattice spacing is a physical dimension of a unit cell within the substrate or top layer used to make the expected, periodic structures.

In addition to the above-described methodology of determining peak spacing and pitch, methods according to embodiments of the invention may also use peak spacing and pitch to indicate a defect in test area 90 and to make corrections to processing equipment 130 (FIG. 5) such as photolithography tool 132 (FIG. 5).

Figure 1:
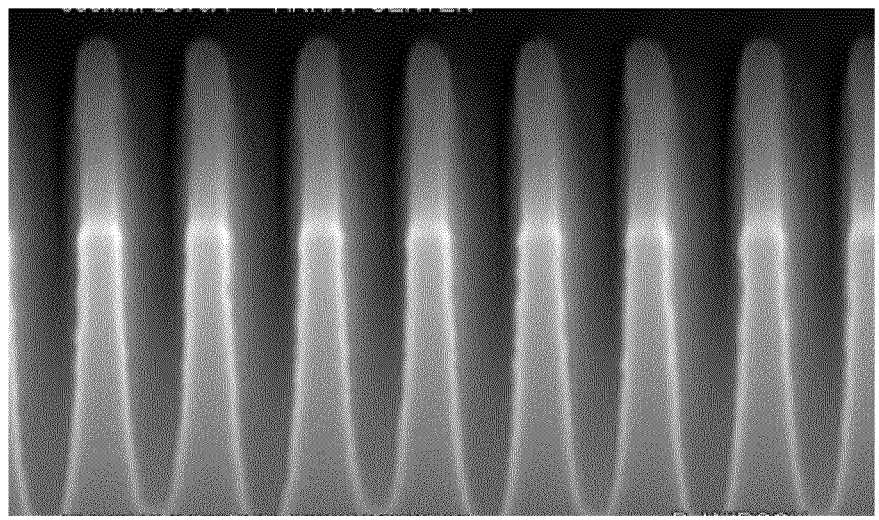
FIG. 1 shows an SEM image of a plurality of equally spaced fins.
Figure 2:
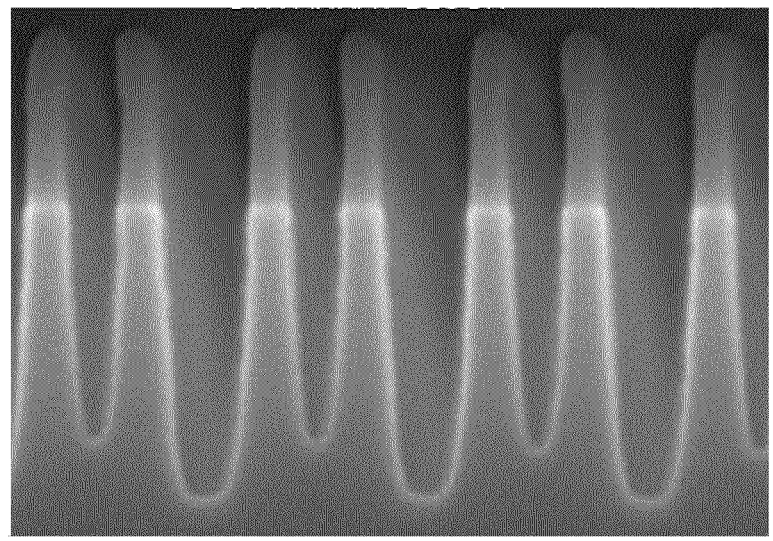
FIG. 2 shows an SEM image of a plurality of fins exhibiting pitch walking

With continuing reference to where expected, periodic structures include fins or gates, and referring to FIG. 7 at A (left side), in process P160, evaluation system 104 may indicate a defect in test area 90 based on the pitch spacing. In particular, for fins or gates (in sub-steps S162 and S167) evaluation system 104 may indicate a pitch walking defect in the test area in response to the pitch being double an expected pitch spacing that is based on a photolithographic mask used to make the test area. More specifically, in sub-step S162, evaluation system 104 may determine whether the pitch for two adjacent spaced structures (within intensity data 120 for the particular ROI defined in process P130) is double an expected pitch (EP) that is based on a photolithographic mask used to make the test area. That is, system 104 determines whether the calculated pitch is equal to or greater than twice the expected pitch (EP). The expected pitch may be based on the photolithographic mask used to make the test area 90 and may be based on at least one of: half the mandrel spacing from the photolithographic mask and process assumptions (PA) defined by minimum gate spacing in a selected technology node. A pitch that is double the expected pitch is indicative of pitch walking as illustrated in FIG. 2. If the calculated pitch is not double the expected pitch, i.e., No at sub-step S162, at sub-step S164, no defect is indicated and the indication of 'no defect' is fed back to processing equipment 130 such as photolithography tool 132 via the host (factory automation software), e.g., through Automated Process Control (APC), at sub-step S166.

If the pitch is double the expected pitch, i.e., Yes at sub-step S162, at sub-step S167, a defect is indicated by evaluation system 104. In addition, at sub-step S168, evaluation system may determine an amount of pitch walking from a ratio of intensities of adjacent peaks via comparison with a calibration curve from a reference dose-stripe wafer. In one example of this technique, a wafer with varying amounts of pitch walking is generated by changing the dose from photolithography tool 132 (FIG. 5). The X-ray beam signal from these samples are calibrated versus the physical pitch determined from cross-sectional TEM images, and saved with photolithography tool 132 (FIG. 5). In sub-step S170, a calibration curve (described above) of intensity ratio versus dose is queried (pulled) from a host photolithography tool 132 (FIG. 5). Although on method has been described, the ratio versus dose calibration curve may be generated using any now known or later developed technique such as but not limited to: modeling, empirical data, etc. In sub-step S166, an adjustment is directed (fed back) to photolithography tool 132 (FIG. 5) to correct for the pitch walking, based on the calibration curve, e.g., increasing or decreasing dose to eliminate the pitch walking.

Returning to FIG. 6 and the right side, bottom sub-steps S146-S152 and process P130 will now be described relative to epitaxial structures and the possibility of merger of these structures. As noted herein, process P130 includes evaluation system 104 identifying intensity peaks in the recordings of the first and second intensities and, based on positions of the intensity peaks relative to the test area, determining a peak spacing between the plurality of expected, periodic structures. In the evaluation of epitaxial merger, however, merger is indicated where pitch spacing is determined as being non-existent, i.e., zero spacing between expected, periodic structures. That is, no pitch spacing indicates adjacent, expected, periodic structures are merged together.

Figure 12:
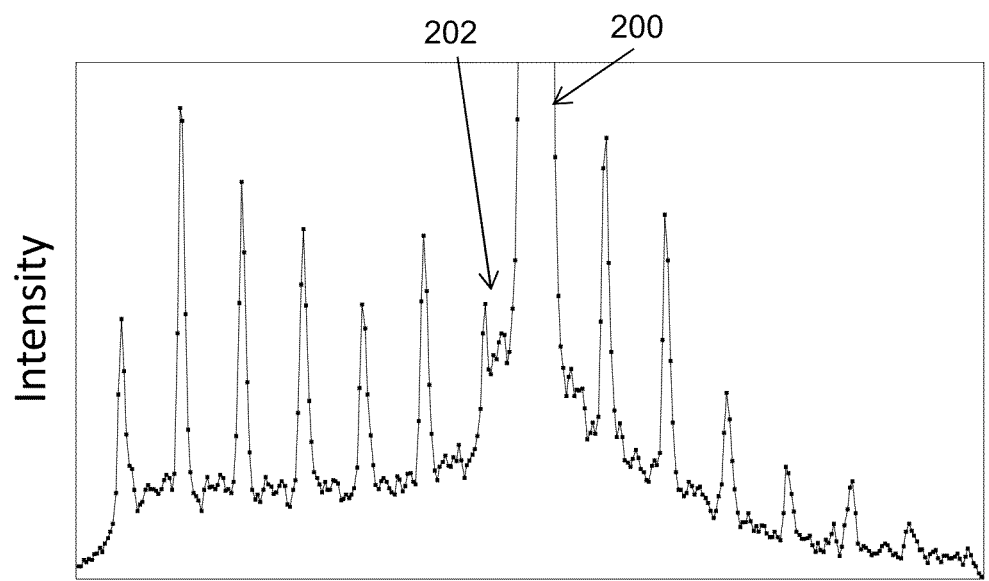
FIG. 12 shows an illustrative graphical representation of peak intensities recorded from a detector for a silicon-based substrate having structures exhibiting no epitaxial merge according to embodiments of the invention.
Figure 13:
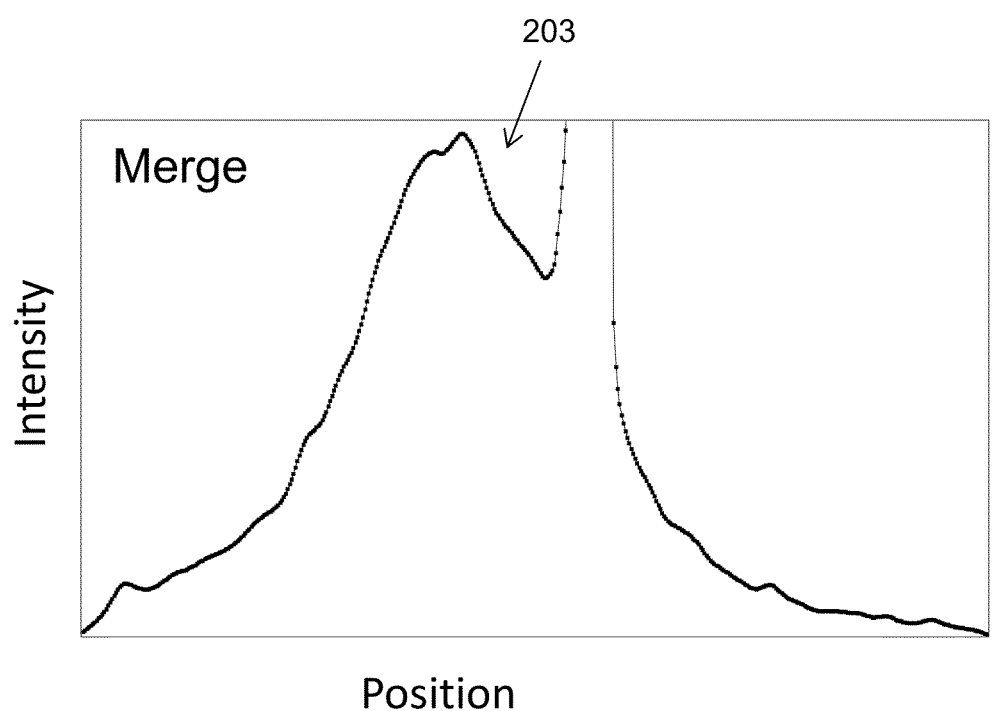
FIG. 13 shows an enlarged view of a peak indicating epitaxial merge according to embodiments of the invention.

In sub-step S146, a relevant region of interest (ROI) of test area 90 can be identified. For epitaxial structures, the ROI of test area 90 can be centered around the offset peak. In this case, the ROI should be chosen with width in h-space representative of epitaxial film thickness and l-space width can be the full measured range. (Similar to ROI for gates (PC), sub-step S134). In sub-step S148, the data is integrated in the l-space and the recordings (line scan) are extracted. FIG. 12 shows an illustrative graphical representation of the recordings of the first and second intensities, i.e., data integrated in L-space and recordings extracted. The graph plots the diffracted intensity versus h or angle, depending on the units used. FIG. 12 shows data for epitaxial structures in test area 90 having an SOI substrate and not exhibiting epitaxial merge. As shown in FIG. 12, the first intensity (substrate peak) 200 is positioned at the center of the graph, and peak 202 occurs left of the substrate peak. As shown in FIG. 13 in an enlarged manner, peak 203, however, is a broad peak, indicating an epitaxial merge.

In sub-step S150, peak positions in the h-space and their intensities are found, i.e., from the intensity data as represented in the graphical representations of FIG. 12. In sub-step S152, the peak spacing is calculated (determined), ignoring the first intensity (substrate peak) if it is in the ROI. As can be discerned by evaluating the graph of FIG. 13, peak spacing is not uniform as there is the only peak 203 present to the side of substrate peak 200. In this situation, identifying peak intensities and peak spacing results in a finding of no peak spacing, indicating epitaxial merge exists. That is, expected, periodic structures have merged into a single structure indicated by a single, broad peak. It is understood that although sub-steps S150 and 152 are described as finding peak intensities and calculating peak spacing, respectively, per merged sub-step S154, they may cumulatively be re-stated as determining epitaxial merge (or merge shape) since multiple peaks may not be ascertainable in the scans where epitaxial merge exists.

As noted herein, in addition to the above-described methodology of determining epitaxial merge, methods according to embodiments of the invention may also use epitaxial merge data to indicate a defect in test area 90 and to make corrections to processing equipment 130 (FIG. 5).

With continuing reference to where expected, periodic structures include epitaxial structures, and referring to FIG. 7 at B (right side), in process P160, evaluation system 104 may indicate a defect in test area 90 based on the epitaxial merge. In particular, at sub-step S172, evaluation system determines whether only one peak is found. That is, evaluation system 104 determines peak spacing for a pair of spaced structures indicating no spacing between two corresponding adjacent peaks 202 (FIG. 13). Depending on the process of record (i.e., what is being built), epitaxial merge may be a defect, or the lack of epitaxial merge may be a defect. In any event, if more than one peak is found, i.e. No at sub-step S172, at sub-step S174, evaluation system 104 indicates epitaxial structures are not merged. At sub-step S176, evaluation system 104 may indicate a defect if the lack of epitaxial merge is not the process of record, i.e., what is expected to be generated. In contrast, if only one broad peak is found, i.e., Yes at sub-step S172, at sub-step S178, evaluation system 104 indicates epitaxial structure is merged. In this case, at sub-step S180, evaluation system 104 may indicate a defect if epitaxial merge is not the process of record. Alternatively, evaluation system 104 may additionally measure a peak full width at half maximum (FWHM) value, and indicate a defect if the calculated FWHM value is not within a desired specification limit, for example, if a large FWHM is measured (compared to substrate peak FWHM~0.0007), then epitaxial film is merged. In this case, evaluation system 104 may feed back to an epitaxy deposition tool 134 of processing equipment to take corrective action.

The above-described methodology can be carried out by evaluation system 104 in-line with semiconductor wafer processing equipment 130 used to manufacture test area 90, and, as described, may include adjusting a setting of photolithography tool 132, epitaxy deposition tool 134 or other tools in semiconductor wafer processing equipment 130 to correct for the defect, where possible. The methodology described herein, in contrast to conventional X-ray diffractometry and conventional metrology techniques, has an experimentally verified precision for the peak spacing of less than approximately +/−1.0 nanometers, and most notably, approximately +/−0.5 nanometers, with a theoretical error on the order of the wavelength (+/−0.17 nm), making it functional for advanced technology nodes. In addition, the X-ray beam diffractometry technique described herein is a non-destructive, non-contact measurement technique. Consequently, each metric is independently defined in the diffraction spectrum for, e.g., pitch walking, critical dimensions (CD), height etc., and is sensitive to the periodicity of the three-dimensional (3D) structure. Further, the methodology described herein functions at all processing levels where periodicity is maintained, i.e., can work for expected, periodic structures at any level. In addition, as described herein, scanning at specific orientations with respect to the length of the expected, periodic structures in embodiments of the invention can: detect and quantify the amount of pitch walking and/or detect the onset of epitaxial merge. The HRXRD techniques described herein can also be used to determine the "pitch walking" of periodic structures (amorphous, poly crystalline or otherwise) which are surrounded by crystalline materials. In addition, per conventional techniques, the results can also be used to detect strain in all 3 dimensions, CD, sidewall angle and height of the structures as well as epitaxial film thickness and composition deposited on the structures.

The foregoing drawings show some of the processing associated according to several embodiments of this disclosure. In this regard, each drawing or block within a flow diagram of the drawings represents a process associated with embodiments of the method described. It should also be noted that in some alternative implementations, the acts noted in the drawings or blocks may occur out of the order noted in the figure or, for example, may in fact be executed substantially concurrently or in the reverse order, depending upon the act involved. Also, one of ordinary skill in the art will recognize that additional blocks that describe the processing may be added.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present disclosure has been presented for purposes of illustration and description, but is not intended to be exhaustive or limited to the disclosure in the form disclosed. Many modifications and variations will be apparent to those of ordinary skill in the art without departing from the scope and spirit of the disclosure. The embodiment was chosen and described in order to best explain the principles of the disclosure and the practical application, and to enable others of ordinary skill in the art to understand the disclosure for various embodiments with various modifications as are suited to the particular use contemplated.

What is claimed is:

1. A method of evaluating a semiconductor wafer, the method comprising:

recording a first intensity of a reflection of an X-ray beam onto a test area on a substrate of the semiconductor wafer at a detector, the recording occurring as the X-ray beam is projected substantially perpendicular to a length of a first plurality of expected, periodic structures in the test area and at an angle defined between the X-ray beam and a surface of the test area;

recording a plurality of second intensities of the reflection of the X-ray beam onto the test area as the X-ray beam is projected onto the test area at a plurality of increments from the angle; and identifying intensity peaks in the recordings of the first and second intensities and, based on positions of the intensity peaks relative to the test area, determining a peak spacing between two adjacent peaks of the plurality of expected, periodic structures.

2. The method of claim 1, wherein the plurality of expected, periodic structures is one of fins and gates, and further comprising:

determining a pitch based on the peak spacing; and indicating a pitch walking defect in the test area in response to the pitch being double an expected pitch spacing that is based on a photolithographic mask used to make the test area.

3. The method of claim 2, wherein the determining pitch includes:

calculating an average peak spacing by averaging a distance between a plurality of adjacent peaks; and calculating the pitch according to the following formula:

$$\text{pitch} = \left(\frac{\text{lattice spacing}}{\sqrt{2} * \text{average peak spacing}}\right),$$

where lattice spacing is a physical dimension of a unit cell within the substrate or the top layer used to make the expected, periodic structures.

4. The method of claim 2, wherein the expected pitch based on the photolithographic mask used to make the test area is based on at least one of: half the mandrel spacing from the photolithographic mask and process assumptions defined by minimum gate spacing in a selected technology node.

5. The method of claim 2, further comprising performing the steps of claim 1 in-line with semiconductor wafer processing equipment used to manufacture the test area, and further comprising adjusting a setting of a photolithography tool in the semiconductor wafer processing equipment to correct for the pitch walking.

6. The method of claim 1, wherein the plurality of expected, periodic structures include epitaxial structures and further comprising, in response to the determined pitch spacing for a pair of spaced structures indicating no spacing between two corresponding adjacent peaks, indicating the test area as including an epitaxial merge defect in the test area.

7. The method of claim 6, further comprising, in response to the indicating the test area as including the epitaxial merge defect, measuring a full width half maximum value of the two adjacent peaks.

8. The method of claim 1, wherein the recording the plurality of second intensities includes positioning the detector at a detector angle relative to the X-ray beam that is twice that of an incident angle of the X-ray beam on the test area, and incrementally changing at least one of the angles to maximize each second intensity at the detector.

9. The method of claim 1, wherein the X-ray beam includes a monochromatic, collimated X-ray beam.

10. The method of claim 1, wherein a precision of the peak spacing determining is less than approximately +/−1.0 nanometers.

11. The method of claim 1, wherein the angle is dependent on a type of the substrate.

12. A system for evaluating a semiconductor wafer, the system comprising:
a computing device for:
receiving a recording of a first intensity of a reflection of an X-ray beam onto a test area on a substrate of the semiconductor wafer, the recording occurring as the X-ray beam is projected substantially perpendicular to a length of a first plurality of expected, periodic structures in the test area and at an angle defined between the X-ray beam and a surface of the test area;
receiving a recording of a plurality of second intensities of the reflection of the X-ray beam onto the test area as the X-ray beam is projected onto the test area at a plurality of increments from the angle; and
identifying intensity peaks in the recordings of the first and second intensities and, based on positions of the intensity peaks relative to the test area, determining a peak spacing between two adjacent peaks of the plurality of expected, periodic structures.

13. The system of claim 12, wherein the plurality of expected, periodic structures is one of fins and gates, and wherein the computing device further:
determines a pitch based on the peak spacing; and
indicates a pitch walking defect in the test area in response to the pitch being double an expected pitch spacing that is based on a photolithographic mask used to make the test area.

14. The system of claim 13, wherein the pitch determining includes the computing device:
calculating an average peak spacing by averaging a distance between a plurality of adjacent peaks; and
calculating the pitch according to the following formula:

$$\text{pitch} = \left(\frac{\text{lattice spacing}}{\sqrt{2} * \text{average peak spacing}}\right),$$

where lattice spacing is a physical dimension of a unit cell within the substrate or the top layer used to make the expected, periodic structures.

15. The system of claim 13, wherein the expected pitch based on the photolithographic mask used to make the test area is based on at least one of: half the mandrel spacing from the photolithographic mask and process assumptions defined by minimum gate spacing in a selected technology node.

16. The system of claim 13, wherein the system is in-line with semiconductor wafer processing equipment used to manufacture the test area, and wherein the computing device further adjusts a setting of a photolithography tool in the semiconductor wafer processing equipment to correct for the pitch walking.

17. The system of claim 12, wherein the plurality of expected, periodic structures are epitaxial structures and wherein the computing device further, in response to the determined pitch spacing for a pair of spaced structures indicating no spacing between two corresponding adjacent peaks, indicates the test area as including an epitaxial merge defect in the test area.

18. The system of claim 12, wherein the X-ray beam includes a monochromatic, collimated X-ray beam.

19. A program product stored on a non-transitory computer-readable medium, which when executed, evaluates a semiconductor wafer, the program product comprising:
program code for recording a first intensity of a reflection of an X-ray beam onto a test area on a substrate of the semiconductor wafer at a detector, the recording occurring as the X-ray beam is projected substantially perpendicular to a length of a first plurality of expected, periodic structures in the test area and at an angle defined between the X-ray beam and a surface of the test area;
program code for recording a plurality of second intensities of the reflection of the X-ray beam onto the test area as the X-ray beam is projected onto the test area at a plurality of increments from the angle; and
program code for identifying intensity peaks in the recordings of the first and second intensities and, based on positions of the intensity peaks relative to the test area, determining a peak spacing between two adjacent peaks of the plurality of expected, periodic structures.

20. The program product of claim 19, wherein the X-ray beam includes a monochromatic, collimated X-ray beam.

\* \* \* \* \*